United States Patent
Haufe et al.

(10) Patent No.: US 7,465,304 B1
(45) Date of Patent: Dec. 16, 2008

(54) ANTERIOR CERVICAL FACET DISCECTOMY SURGERY KIT AND METHOD FOR ITS USE

(75) Inventors: Scott M. W. Haufe, Santa Rosa Beach, FL (US); Anthony R. Mork, Santa Rosa Beach, FL (US)

(73) Assignee: Spine Design, Inc., DeFuniak Springs, FL (US)

( * ) Notice: Subject to any disclaimer, the term of this patent is extended or adjusted under 35 U.S.C. 154(b) by 509 days.

(21) Appl. No.: 10/412,772

(22) Filed: Apr. 14, 2003

(51) Int. Cl.
*A61B 17/00* (2006.01)

(52) U.S. Cl. .................. 606/79; 606/167; 606/170; 606/179

(58) Field of Classification Search .......... 606/79, 606/167, 170, 179; 604/158, 159, 161, 164.01, 604/164.106
See application file for complete search history.

(56) References Cited

U.S. PATENT DOCUMENTS

| | | | |
|---|---|---|---|
| 3,312,220 A | 4/1967 | Eisenberg | |
| 3,598,108 A | * 8/1971 | Jamshidi et al. | 600/567 |
| 3,788,320 A | 1/1974 | Dye | |
| 4,141,362 A | 2/1979 | Wurster | |
| 4,573,448 A | 3/1986 | Kambin | |
| 4,696,308 A | * 9/1987 | Meller et al. | 600/567 |
| 4,961,740 A | 10/1990 | Ray et al. | |
| 4,973,312 A | 11/1990 | Andrew | |
| 5,015,247 A | 5/1991 | Michelson | |
| 5,062,845 A | 11/1991 | Kuslich et al. | |
| 5,135,525 A | * 8/1992 | Biscoping et al. | 604/512 |
| 5,169,400 A | 12/1992 | Muhling et al. | |
| 5,195,541 A | 3/1993 | Obenchain | |
| 5,203,781 A | 4/1993 | Bonati | |
| 5,241,972 A | 9/1993 | Bonati | |
| 5,242,427 A | 9/1993 | Bilweis | |
| 5,263,955 A | 11/1993 | Baumgart et al. | |
| 5,269,797 A | 12/1993 | Bonati et al. | |
| 5,290,279 A | 3/1994 | Bonati et al. | |
| 5,306,274 A | 4/1994 | Long | |
| 5,343,543 A | 8/1994 | Novak et al. | |
| 5,391,152 A | 2/1995 | Patterson | |
| 5,423,824 A | * 6/1995 | Akerfeldt et al. | 606/80 |
| 5,437,661 A | 8/1995 | Rieser | |
| 5,439,464 A | 8/1995 | Shapiro | |
| 5,445,639 A | 8/1995 | Kuslich et al. | |

(Continued)

OTHER PUBLICATIONS

Spine 2002 Abstract of pp. 1887-1895.

(Continued)

*Primary Examiner*—Eduardo C Robert
*Assistant Examiner*—James L Swiger, III
(74) *Attorney, Agent, or Firm*—Banner & Witcoff, Ltd.

(57) ABSTRACT

A surgical kit is used for performing an anterior cervical disectomy, the surgical kit having a sheath that is inserted into a mammal by using a bullet coupled to the sheath and impacting on the bullet. Various cutters, including a cervical cutter having a drill tip end, a serrated cutter having an enclave for receiving cutting spoils therein, and a deburrment cutter having a burr end, are insertable through the sheath for cutting bone and disc matter. An impactor can be used to move the sheath within the mammal during use of the serrated cutter and deburrment cutter without the need to remove either tool. A pituitaries is used to remove loose bone and disc material.

18 Claims, 5 Drawing Sheets

U.S. PATENT DOCUMENTS

| | | | |
|---|---|---|---|
| 5,472,426 | A | 12/1995 | Bonati et al. |
| 5,665,092 | A | 9/1997 | Mangiardi et al. |
| 5,665,093 | A | 9/1997 | Atkins et al. |
| 5,772,594 | A | 6/1998 | Barrick |
| 5,772,678 | A | 6/1998 | Thomason et al. |
| 5,810,821 | A | 9/1998 | Vandewalle |
| 5,810,826 | A * | 9/1998 | Åkerfeldt et al. ............... 606/80 |
| 5,836,949 | A | 11/1998 | Campbell, Jr. et al. |
| 5,860,973 | A | 1/1999 | Michelson |
| 5,868,749 | A | 2/1999 | Reed |
| 6,004,326 | A * | 12/1999 | Castro et al. .................. 606/99 |
| 6,068,630 | A | 5/2000 | Zucherman et al. |
| 6,074,423 | A | 6/2000 | Lawson |
| 6,096,038 | A | 8/2000 | Michelson |
| 6,176,825 | B1 | 1/2001 | Chin et al. |
| 6,261,586 | B1 | 7/2001 | McKay |
| 6,264,651 | B1 | 7/2001 | Underwood et al. |
| 6,264,675 | B1 | 7/2001 | Brotz |
| 6,287,313 | B1 | 9/2001 | Sasso |
| 6,395,007 | B1 | 5/2002 | Bhatnagar et al. |
| 6,447,512 | B1 | 9/2002 | Landry et al. |
| 6,540,753 | B2 * | 4/2003 | Cohen ......................... 606/99 |
| 6,974,480 | B2 | 12/2005 | Messerli et al. |
| 2001/0027320 | A1 | 10/2001 | Sasso |
| 2001/0034535 | A1 | 10/2001 | Schultz |
| 2002/0026192 | A1 | 2/2002 | Schmiel et al. |
| 2002/0032447 | A1 | 3/2002 | Weikel et al. |
| 2002/0091387 | A1 | 7/2002 | Hoogland |
| 2002/0091390 | A1 | 7/2002 | Michelson |
| 2002/0128716 | A1 | 9/2002 | Cohen et al. |
| 2002/0151895 | A1 | 10/2002 | Soboleski et al. |
| 2005/0159746 | A1 | 7/2005 | Grob et al. |
| 2008/0015565 | A1 | 1/2008 | Davison |

OTHER PUBLICATIONS

Mt. Sionai J Med 1994 Abstract of pp. 233-238.

* cited by examiner

ANTERIOR CERVICAL FACET DISCECTOMY SURGERY KIT AND METHOD FOR ITS USE

BACKGROUND OF THE INVENTION

1. Field of the Invention

The present invention relates to a kit of surgical tools for performing a minimally invasive anterior cervical disectomy and the method for the tools' use.

2. Background of the Prior Art

The human spine is formed from 33 vertebrae divided into five different regions, the cervical, dorsal, lumbar, sacral, and coccygeal, in descending order. Of the five regions, the vertebrae of the upper three remain separated through the life of a person while the lower two fuse in an adult to form two bones, the sacral vertebrae forming the sacrum and the coccygeal vertebrae forming the coccyx. The human spine, which is a weight bearing column, may be afflicted with a variety of ailments such as a disc herniation which may compress the spinal cord or the nerve roots leading to pain, loss of function, and in severe cases, complete paralysis of the legs with an attendant loss of bowel and bladder control. Surgical intervention to remove the offending discal tissue is the prescribed course of treatment. Traditionally, such procedures were not only difficult, but oftentimes dangerous. Traditional surgical techniques called for a large incision to be made, the appropriate disectomy to be performed, and the patient to be closed. Such a surgical procedure is extremely invasive causing substantial trauma to the intervening tissue and leading to an extended post operative recovery period which is typically accompanied by substantial discomfort and pain. Additionally, substantial scarring of the patient occurs and in the case of a cervical disectomy, such scarring is not easily disguised by the patient. As often the amount of post operative discomfort and the size of the scar are the only objective criteria used by the patient to judge the quality of the surgeon's work, it is advantageous to reduce the size of the incision made and the scar left behind.

Toward that end and in order to address the other drawbacks of traditional surgical procedures for curing disc herniation, minimally invasive procedures have been developed wherein the spine is approached by making one or more small incisions into the patient and placing a sheath into the body via each incision and passing various instruments through the sheaths in order to gain mechanical access to the desired area. Such access may include placement of video cameras into the body cavity in order to allow the surgeon to have visual access to the affected area as well as placing deburrment and removal tools into the body cavity in order to extricate the offending disc material. The sheaths protect the surrounding blood vessels and organs during traversal of the body by the various instruments.

The use of minimally invasive surgical procedures has greatly reduced the complexity and inherent danger associated with spinal surgery. Additionally, many procedures are performed under local anesthesia wherein the patient maintains consciousness resulting in a dramatic decrease in post operative discomfort of the patient and compression of the post operative recovery period. Furthermore, the scarring of the patient is dramatically reduced with the surgical procedure leaving only one or more small wounds which tend to bypass scrutiny by the casual observer even for a cervical procedure. Accordingly, minimally invasive surgical techniques for dissecting offending material from the spine have achieved wide acceptance and advances in various minimally invasive techniques are constantly being made.

Of the various disectomy procedures that are performed, perhaps the trickiest is that of the cervical disectomy. Unlike the back of a person, the neck is relatively narrow and vital arteries and organs, including the carotid, the jugular, the trachea, and the esophagus, are bunched much more tightly. This places an even greater burden on the surgeon to exercise the utmost care in performing the surgery so as to not cause trauma to these organs and arteries.

Providing the surgeon with the appropriate tools to perform the cervical disectomy, enables the surgeon to achieve a high level of surgical success while minimizing the risk to the patient. Such tools must be effective for all aspects of the procedure including placement of the initial incision and insertion of the protective sheath into the neck, deburrment of the offending tissue, and extraction of the offending tissue. The tools must be simple in design yet elegant in operation without the need for undue indwelling of the tools within the patient.

SUMMARY OF THE INVENTION

The anterior cervical disectomy surgery kit and method for its use of the present invention address the aforementioned needs in the art. The tools of the surgery kit are effective for all aspects of the procedure including placement of the initial incision and insertion of the protective sheath into the neck, deburrment of the offending tissue, and extraction of the offending tissue, the surgeon being able to achieve a high level of surgical success while minimizing the risk to the patient. The tools are simple in design yet elegant in operation eliminating the need for undue indwelling of the tools within the patient.

The anterior cervical disectomy surgery kit and method for its use of the present invention are comprised of a sheath having a hollow core, a proximal end and a distal end such that the distal end is passed through the body of a mammal, the sheath also having a cap located on its distal end. A serrated cutter has a proximal end and a distal end that is serrated, such that the distal end of the serrated cutter is inserted into the hollow core of the sheath and into the mammal. A cap is removably attached to the proximal end of the serrated cutter for turning the serrated cutter upon insertion into the sheath. An impactor has a hollow core such that the distal end of the serrated cutter is received within the impactor's hollow core and the impactor abuts against the cap of the sheath. The serrated cutter has a hollow core for passage of a guide wire therethrough. The distal end of the serrated cutter has an opening leading to a hollow enclave for capturing spoils resulting from the bone and disc cutting process. The sheath is inserted anterior of the neck of the mammal at an angle of about 45 degrees such that the sheath passes through the neck just behind a trachea and an esophagus within the neck and just medial to a carotid and a jugular within the neck. A bullet has a proximal end, a distal end, and a hollow core for passage of a guide wire therethrough, the proximal end of the bullet having a cap thereon, such that the bullet and the sheath are coupled by passing the distal end of the bullet into the hollow core of the sheath proximate the proximal end of the sheath and passing the bullet through the hollow core of the sheath such that the distal end of the bullet seats within the distal end of the sheath. The distal end of the bullet is pointed and extends beyond the distal end of the sheath whenever the sheath and the bullet are coupled. The proximal end of the sheath is locked in dovetail fashion with the proximal end of the bullet when the sheath and the bullet are coupled. A hammer is used for impacting on the impactor and the cap of the bullet. A cervical cutter has a proximal end with a handle thereon, and a distal end that is drill bit tipped, such that the distal end of the cervical cutter is inserted into the hollow core of the sheath and into the mammal for cutting bone and disc. A deburrment cutter has a proximal end, and a distal end that has a burr thereon, such that the distal end of the deburrment cutter is inserted into the hollow core of the sheath and into the mammal for deburring, either initially or after use of the serrated cutter or the cervical cutter, bone and disc. A cap is removably attached to the proximal end of the deburrment cutter such that when this cap is removed from the deburrment cutter, the proximal end of the deburrment cutter is received within the hollow core of the impactor. The deburrment cutter has a hollow core for passage of the guide wire therethrough. A pituitaries has a handle end and a grasping end, such that the grasping end is inserted into the hollow core of the sheath and into the mammal for retrieving bone and disc fragments.

BRIEF DESCRIPTION OF THE DRAWINGS

Similar reference numerals refer to similar parts throughout the several views of the drawings.

DESCRIPTION OF THE PREFERRED EMBODIMENT

Figure 1:
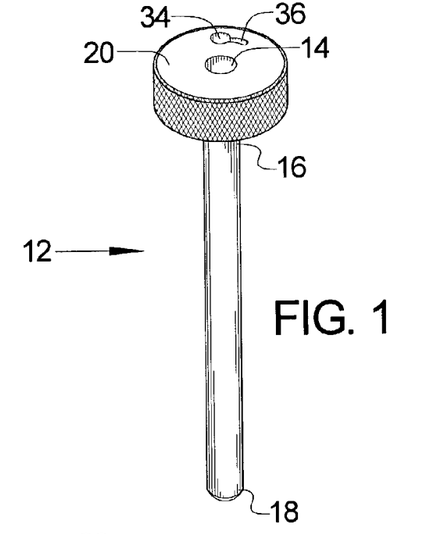
FIG. 1 is a perspective view of the sheath used with the anterior cervical disectomy surgery kit and method for its use of the present invention.

Referring now to the drawings, it is seen that the anterior cervical disectomy surgery kit and method for its use of the present invention is comprised of a sheath 12 that has a first hollow core 14 and also has a first proximal end 16 and a first distal end 18. A first cap 20, which may be knurled for better gripping thereof, is located on the sheath's proximal end 14. The distal end 18 of the sheath 12 is slightly beveled. The sheath 12 is made from any appropriate bioacceptable material such as metal or plastic and must be able to endure mild hammering and must be relatively thin, on the order of less than about 1 millimeter in thickness, yet strong enough to not easily bend. The diameter of the sheath 12 is on the order of just a few millimeters and the inside diameter of the first hollow core 14 may be approximately 5 millimeters with the outside diameter of the sheath 12 being approximately 6 millimeters, although both the inside diameter and the outside diameter of the sheath 12 may be greater or less than the above values in keeping within the scope and spirit of the present invention 10.

Figure 2:
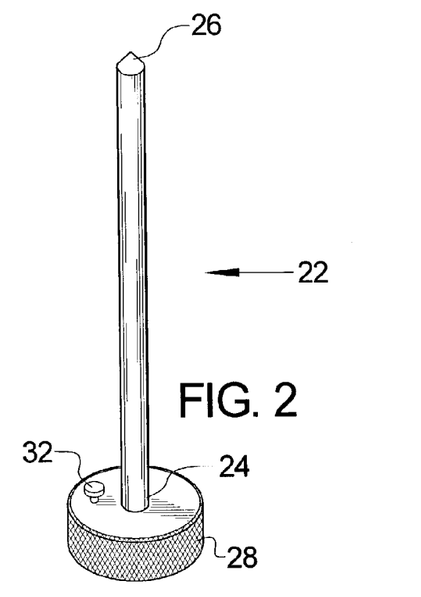
FIG. 2 is a perspective view of the bullet used with the anterior cervical disectomy surgery kit and method for its use.

A bullet 22 has a second proximal end 24 and a second distal end 26. A second cap 28 is located on the proximal end 24 of the bullet 22, which second cap 28 may also be knurled for better gripping thereof. The second cap 28 may be about the size of the first cap 20. The distal end 26 of the bullet 22 is pointed. The bullet 22 has a second hollow core 30 which may be on the order of less than 1 millimeter in diameter although the diameter may be more or less than this value. The bullet 22 is also made from a bioacceptable material such as metal or plastic and may be made from the same material as the sheath 12 and must also be able to endure hammering thereupon.

Figure 3:
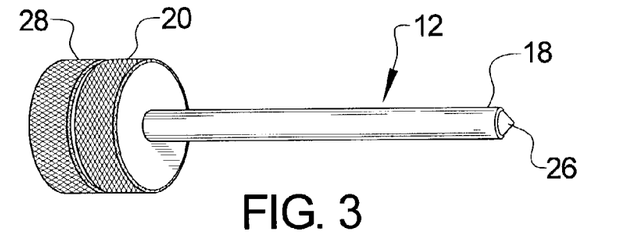
FIG. 3 is a perspective view of the bullet and the sheath mated together.
Figure 5:
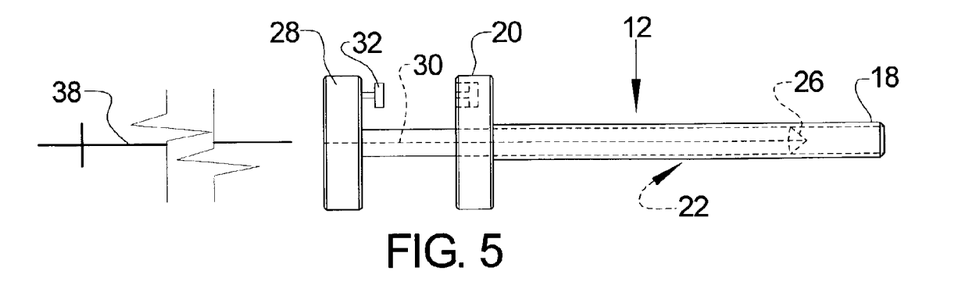
FIG. 5 is a side view of the bullet and the sheath illustrating the interior detail.

The sheath 12 and the bullet 22 are coupled by passing the second distal end 26 of the bullet 22 into the first hollow core 14 at the first proximal end 16 of the sheath 12 and passing the bullet 22 through the first hollow core 14 such that the second distal end 26 of the bullet 22 seats within the first distal end 18 of the sheath 12. In such a configuration, the second distal end 26 of the bullet 22 extends beyond the first distal end 18 of the sheath 12. Once the bullet 22 is received within the sheath 12 the two members 12 and 22 are locked to one another. This can be accomplished by providing a standard dovetailing arrangement wherein a peg 32 is provided on the second proximal end 24 of the bullet 22 which peg 32 is received within a relatively wide opening 34 located on the first proximal end 16 of the sheath 12 and the bullet 22 is twisted in order to pass the peg 32 into the relatively smaller restricted area 36 on the proximal end 16 of the sheath 12 thereby locking the bullet 22 to the sheath 12. The peg and openings can be reversed such that the peg is located on the sheath and the openings located on the bullet. Additionally, other locking mechanisms may also be used for locking the sheath 12 with the bullet 22.

Figure 4:
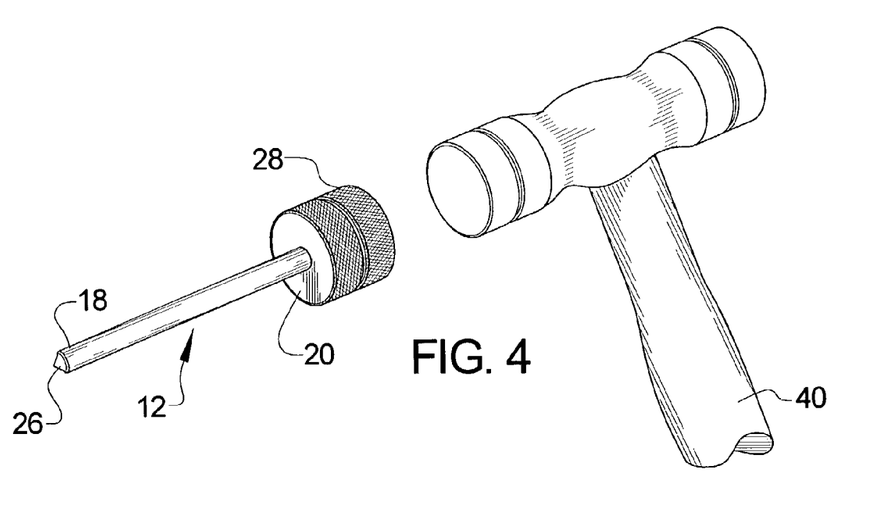
FIG. 4 is a perspective view of the bullet and the sheath mated together accompanied by the hammer used for impacting the bullet.
Figure 6:
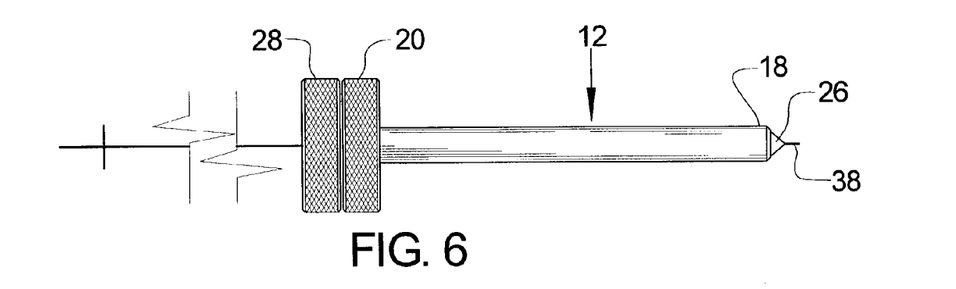
FIG. 6 is a side view of the bullet and the sheath with a guide wire passing therethrough.

A guide wire or K-wire 38 is passed through the second hollow core 30 of the bullet 22. The coupled sheath 12 and bullet 22 are passed through a mammalian body to a desired area wherein a surgical procedure is performed. This is accomplished by hammering on the proximal end 24 of the bullet 22. The pointed distal end 22 of the bullet 22 helps facilitate passage of the bullet 22 through the body, the hammer 40 being of any appropriate design. As the bullet 22 passes through the body, the sheath 12 coupled to the bullet 22 also passes through the body of the patient.

In a cervical disectomy procedure, the coupled sheath 12 and the bullet 22 are positioned at the front of the neck N of the patient P at about 45 degrees to the front midline of the neck such that the sheath 12 and bullet 22 pass through the neck N just behind the trachea and esophagus and just medial to the carotid and jugular. Once the coupled sheath 12 and bullet 22 are in proper position within the patient's body, the K-wire 38 is secured and the bullet 22 is unlocked from the sheath 12, decoupled from the sheath 12, and removed from the body with the K-wire 38 remaining in the patient and passing through the sheath 12. Additional sheaths 12 may be inserted into the patient's body as needed such as to give the surgeon additional visual access to surgical area of the patient P.

Figure 7:
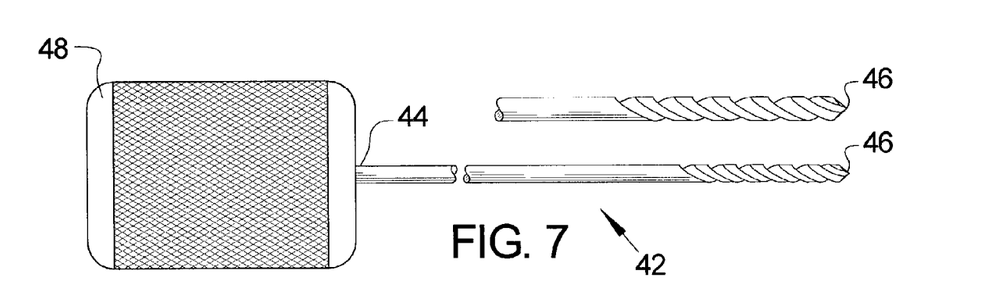
FIG. 7 is a side view of the cervical cutters used with the anterior cervical disectomy surgery kit and method for its use of the present invention.
Figure 8:
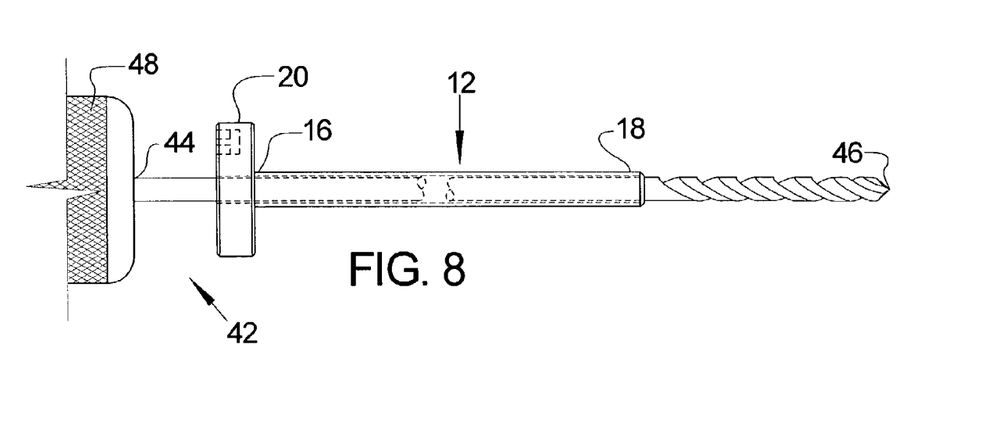
FIG. 8 is a side view of the cervical cutter passed through the sheath.
Figure 9:
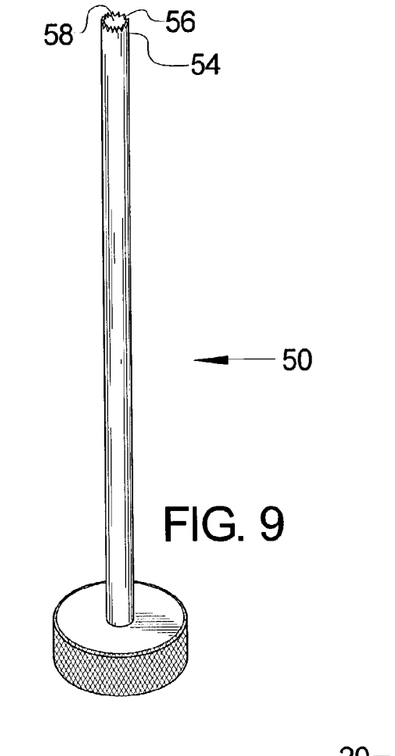
FIG. 9 is a perspective view of the serrated cutter used with the anterior cervical disectomy surgery kit and method for its use, with the serrated cutter mated to its cap.
Figure 10:
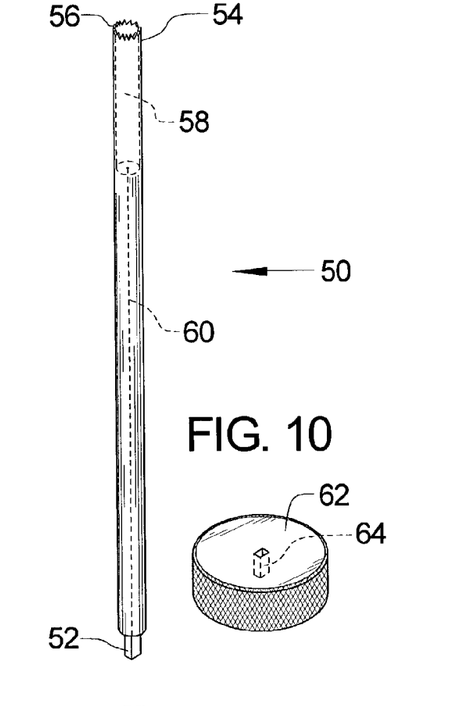
FIG. 10 is a perspective view of the serrated cutter illustrating its interior detail as well as illustrating the detail of the cap.
Figures 11, 12:
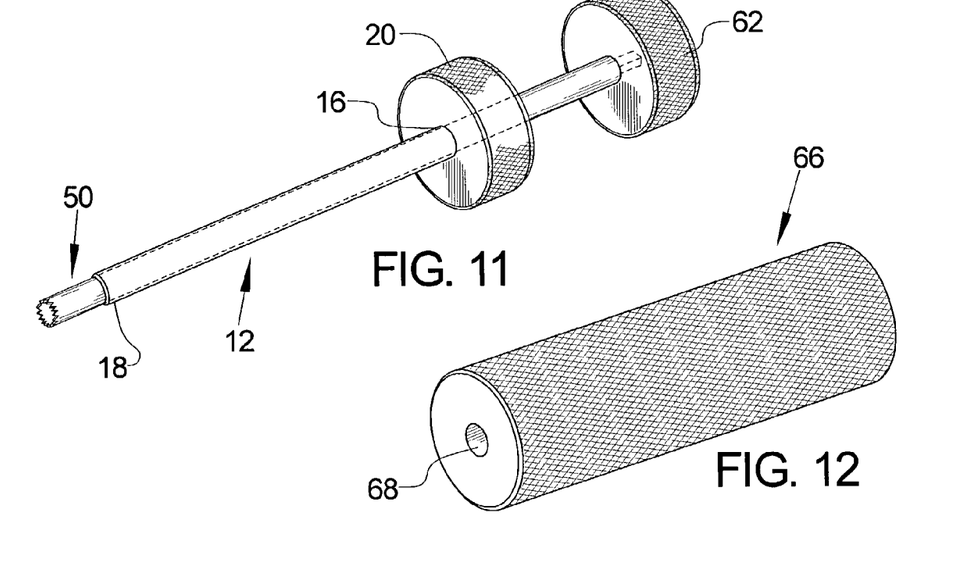
FIG. 11 is a perspective view of the serrated cutter passed through the sheath.
FIG. 12 is a perspective view of the impactor used with the anterior cervical disectomy surgery kit and method for its use.
Figure 13:
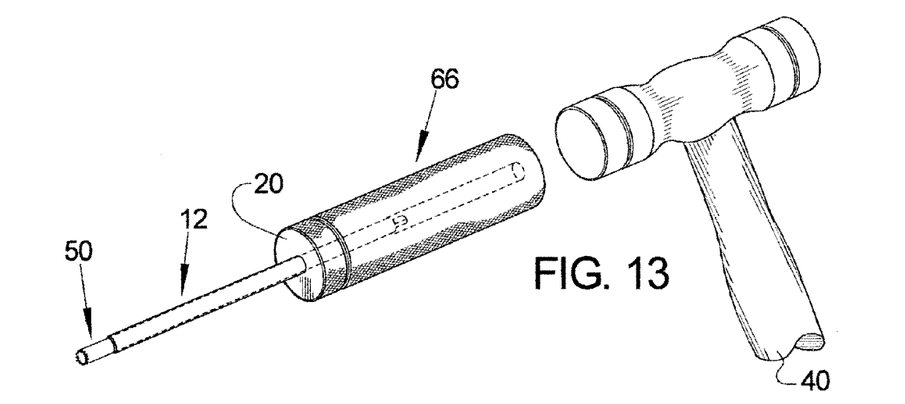
FIG. 13 is a perspective view of the impactor being used with the serrated cutter.

Thereafter, the surgeon uses one or more cutting tools in order to cut disc and bone for removal from the patient P. The various cutting tools are illustrated in FIGS. 7-15, and with specific reference to FIGS. 7 and 8 there is illustrated a cervical cutter 42 that has a third distal end 44 and a third proximal end 46. The third distal end 46 of the cervical cutter 42 is drill bit tipped and is front cutting and has a cutting point to the end of the tip. The third proximal end 42 of the cervical cutter 42 has an appropriate handle 48 thereon which may be knurled in order to afford the surgeon a better grip of the cutter 42. As illustrated in FIG. 7, the distal end 46 of the cervical cutter 42 may come in different diameters, for example 1/8 or 3/16 inches in diameter, although other diameters are possible. The length of the cervical cutter 42 is sufficient in order to allow the handle 48 of the cutter to be spaced sufficient distance from the sheath 12 so that as the cutter 42 descends into the disc or bone during the cutting procedure, and thus further into the sheath 12, the sheath 12 does not interfere with the handle 48. In order to use the cervical cutter 42, the distal end 46 of the cutter is inserted through the proximal end 14 of the sheath until the pointed distal end 46 of the cutter 42 reaches the point of cutting, at which point the surgeon rotates the cutter 42 via the handle 48. Once use of this cutter 42 is no longer needed, the cutter 42 is removed from the sheath 12.

A serrated cutter 50 is illustrated in FIGS. 9-15, which cutter 50 has a fourth proximal end 52 and a fourth distal end 54, which distal end 54 has serrations 56 thereon. The distal end 54 of the serrated cutter 50 is open and leads to a hollow enclave 58 that extends toward the proximal end 52 of this cutter 50. The serrated cutter 50 has a third hollow core 60 which may be on the order of less than 1 millimeter in diameter although the diameter may be more or less than this value, the third hollow core 60 allowing passage of the K-wire 38 therethrough. A third cap 62 is removably attached to the proximal end 52 of the serrated cutter 50. As seen, the third cap 62 has a fourth hollow core 64, which hollow core 64 is non-circular in shape and the proximal end 52 of the serrated cutter 50 has a similar shape in order to facilitate a keyed attachment of the cap 62 to the cutter 50 and thereafter permit turning of the cutter 50 via the cap 62. The serrated cutter 50 is several inches longer than the length of the sheath 12. In use, the third cap 62 is attached to the proximal end 52 of the cutter 50 and the distal end 54 of the serrated cutter 50 is passed over the K-wire 38 and into the proximal end 14 of the sheath 12 and passed through the sheath 12 until the cutter 50 reaches the desired point of procedure. The cutter 50 is rotated via the third cap 62 such that the serrations cut into bone and disc matter. Much of the cutaway spoils of the bone and disc being cut are received within the hollow enclave 58 of the cutter 50 for subsequent removal from the body of the patient P when the cutter 50 is removed. Oftentimes it is desirable to move the sheath 12 in conjunction with the dissension of the serrated cutter 50 deeper into the body. In order to accomplish this movement of the sheath 12, an impactor 66 is provided, the impactor 66 having a fourth hollow core 68, the diameter of this hollow core 68 being slightly greater than the outside diameter of the serrated cutter 50. The impactor 66 is several inches long in order to afford the surgeon a good grip thereon and may be knurled. The third cap 62 is removed from the serrated cutter 50 and the impactor is positioned so as to slide over the serrated cutter 50 and abut against the first cap 20 of the sheath 12. The hammer 40 is used to strike the end of the impactor 66 that is opposite the end abutting the sheath 12, which hammering force transfers to the sheath 12 causing movement of the sheath 12. As the serrated cutter 50 is within the first hollow core 14 of the sheath 12 and the fourth hollow core 68 of the impactor 66 and slides within these hollow cores 14 and 68, the hammering force does not transfer to the serrated cutter 50 and therefore the cutter 50 does not move as a result of the hammering. Once the sheath 12 is appropriately repositioned, the impactor 66 is removed from about the serrated cutter 50 and the third cap 62 is replaced onto the proximal end 52 of the cutter 50, and the surgeon once again cuts bone and disc matter as desired. Accordingly, the sheath 12 is movable within the patient's body without the need to remove and thereafter replace the serrated cutter 50.

Figures 14, 15:
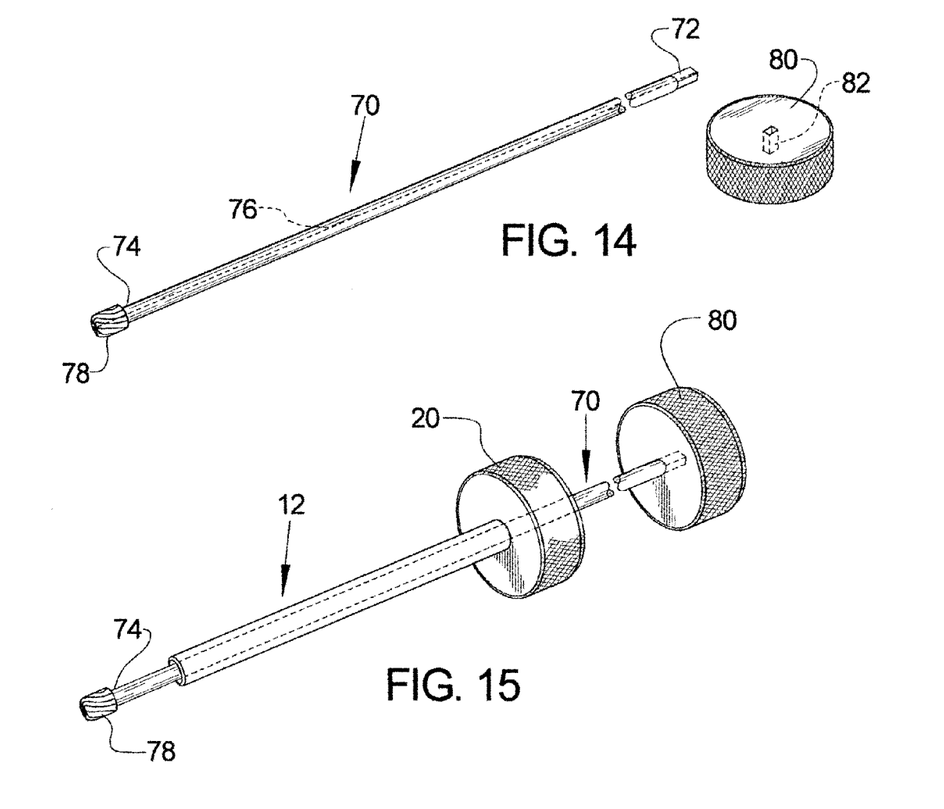
FIG. 14 is a perspective view of the deburrment tool and its cap that are used with the anterior cervical disectomy surgery kit and method for its use.
FIG. 15 is a perspective view of the deburrment cutter passed through the sheath.
Figure 16:
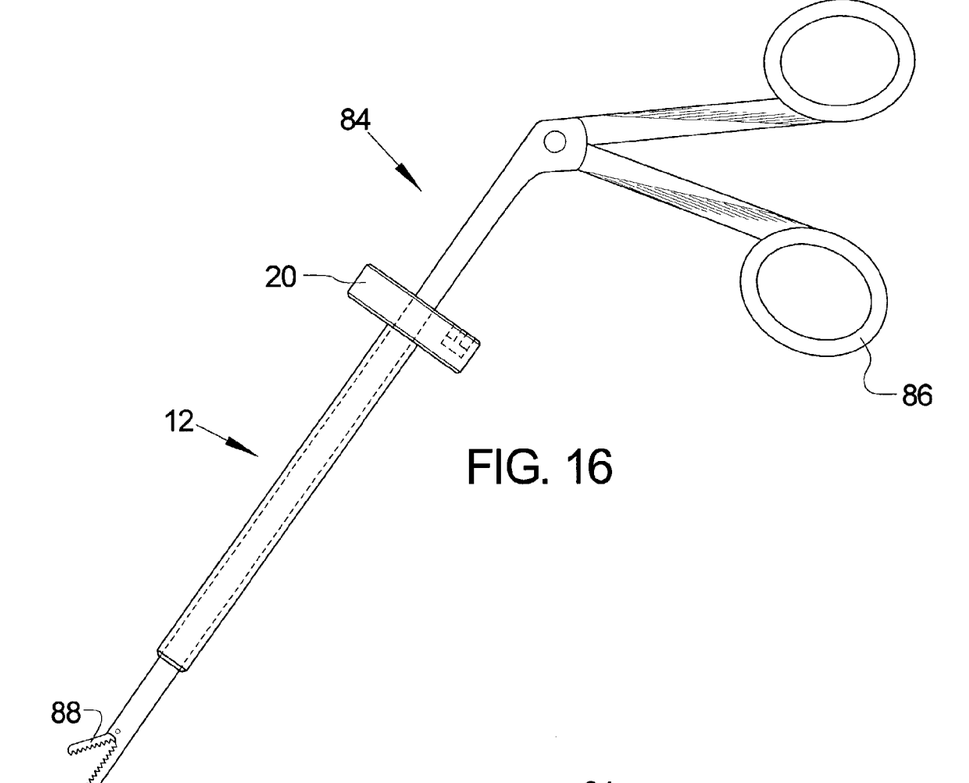
FIG. 16 is a side view of the pituitaries used with the anterior cervical disectomy surgery kit and method for its use, the pituitaries passed through the sheath.
Figure 17:
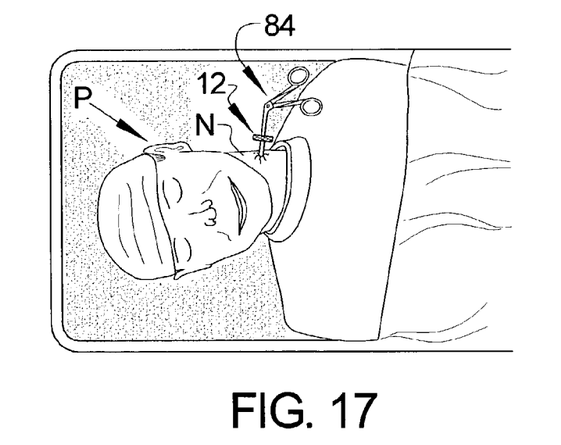
FIG. 17 is an environmental view of the pituitaries being used on a patient.

A deburrment cutter 70 is illustrated in FIGS. 14 and 15, the deburrment tool having a fourth proximal end 72 and a fourth distal end 74. The deburrment cutter 70 has a fifth hollow core 76 which may be on the order of less than 1 millimeter in diameter although the diameter may be more or less than this value, the fifth hollow core 76 allowing passage of the K-wire 38 therethrough. A burr 78 is located on the fourth distal end 74 of the deburrment cutter 70, while a fourth cap 80 is removably attached to the proximal end of the deburrment cutter 70. As seen, the fourth cap 80 has a fifth hollow core 82, which hollow core 82 is non-circular in shape and the proximal end 72 of the deburrment cutter 70 has a similar shape in order to facilitate a keyed attachment of the cap 80 to the cutter 70 and thereafter permit turning of the cutter 70 via the cap 80. It is recognized that the same cap may be used for both the serrated cutter 50 and the deburrment cutter 70 although most surgeons prefer each tool to have its own cap.

The deburrment cutter 70 is several inches longer than the length of the sheath 12. In use, the fourth cap 80 is attached to the proximal end 72 of the cutter 70 and the distal end 74 of the deburrment cutter 70 is passed over the K-wire 38 and into the proximal end 14 of the sheath 12 and passed through the sheath 12 until the cutter 70 reaches the desired point of procedure. The cutter 70 is rotated via the third cap 80 such that the burr 76 burrs away jagged edges and helps smooth out bone and disc matter. Oftentimes it is desirable to move the sheath 12 in conjunction with the use of the deburrment cutter 70. In order to accomplish this movement of the sheath 12, the fourth cap 80 is removed from the deburrment cutter 70 and the impactor 66 is positioned so as to slide over the deburrment cutter 70 and abut against the first cap 20 of the sheath 12. The hammer 40 is used to strike the end of the impactor 66 that is opposite the end abutting the sheath 12, which hammering force transfers to the sheath 12 causing movement of the sheath 12. As the deburrment cutter 70 is within the first hollow core 14 of the sheath 12 and the fourth hollow core 68 of the impactor 66 and slides within these hollow cores 14 and 68, the hammering force does not transfer to the deburrment cutter 70 and therefore the cutter 70 does not move as a result of the hammering. Once the sheath 12 is appropriately repositioned, the impactor 66 is removed from about the deburrment cutter 70 and the fourth cap 80 is replaced onto the proximal end 72 of the cutter 70, and the surgeon once again deburrs bone and disc matter as desired. Accordingly, the sheath 12 is movable within the patient's body without the need to remove and thereafter replace the deburrment cutter 70.

As seen in FIGS. 14 and 15, a pituitaries 84, of standard design known in the art, is provided with the surgical kit, the pituitaries 84 having a handle end 86 form manipulation by the surgeon and a grasping end 88 for retrieval of bone and disc matter, such that the grasping end 88 of the pituitaries 84 is passed through the sheath 12 in order to remove bone and disc matter from the surgical sight. The pituitaries 84 can be used at the start of the surgical procedure after the sheath 12 is in place and the bullet 22 is removed therefrom, in order to remove loose disc and bone that may have accumulated prior to the surgical procedure or the pituitaries 84 can be used as bone and disc are cut away during the surgical procedure by one of the cutting tools.

While the invention has been particularly shown and described with reference to an embodiment thereof, it will be appreciated by those skilled in the art that various changes in form and detail may be made without departing from the spirit and scope of the invention.

We claim:

1. A method for performing an anterior cervical discectomy within a neck of a mammal comprising the steps of:
    passing a distal end of a sheath into the neck of the mammal, the sheath having a hollow core and a proximal end with a first cap thereon;
    attaching a second cap to a serrated cutter on a proximal end of the serrated cutter, the serrated cutter also having a distal end with an edge on the most distal portion thereof, the edge having a plurality of serrations formed therein;
    inserting the serrated cutter distal end into the hollow core of the sheath while the sheath is in the mammal neck and cutting bone or disc of the mammal by turning the serrated cutter using the second cap;
    removing the second cap from the serrated cutter while the serrated cutter is in the sheath hollow core and while the sheath is in the mammal neck;
    receiving the proximal end of the serrated cutter within a hollow core of an impactor while the serrated cutter is in the sheath hollow core and while the sheath is in the mammal neck, such that the impactor slides over the serrated cutter and abuts against the first cap on the sheath, the impactor hollow core having a diameter greater than the serrated cutter; and
    placing an impact force onto the impactor so as to transfer said impact force to the sheath and not to the serrated cutter.

2. The method of claim 1, wherein inserting the serrated cutter distal end into the sheath hollow core includes passing the serrated cutter over a guide wire passed through a hollow core of the serrated cutter.

3. The method of claim 1, wherein the serrated cutter distal end has an opening leading to a hollow enclave, and wherein cutting bone or disc of the mammal by turning the serrated cutter includes receiving cutaway spoils of bone and disc within the hollow enclave, and further comprising:
    removing the serrated cutter from the sheath and from the mammal neck while the cutaway spoils are retained within the hollow enclave.

4. The method of claim 1, wherein placing an impact force on the impactor includes impacting the impactor with a hammer.

5. The method of claim 1, wherein passing the sheath distal end into the mammal neck includes inserting the sheath anterior of the mammal neck at an angle of about 45 degrees such that the sheath passes through the neck just behind a trachea and an esophagus within the neck and just medial to a carotid and a jugular within the neck.

6. The method of claim 1 further comprising the steps of:
    inserting a distal end of a bullet into the sheath hollow core at the proximate end of the sheath and passing the bullet through the sheath hollow core such that the bullet distal end seats within the sheath distal end.

7. The method of claim 6, wherein the bullet distal end is pointed and inserting the distal end of a bullet into the sheath hollow includes passing the bullet through the sheath hollow core such that the bullet distal end extends beyond the sheath distal end.

8. The method of claim 6 further comprising the step of locking the sheath proximal end with a bullet proximal end.

9. The method of claim 6 further comprising the step of locking the sheath proximal end in dovetail fashion with a bullet proximal end.

10. The method of claim 6, wherein the bullet has a third cap on a bullet proximal end, and wherein passing a distal end of the sheath into the mammal neck includes impacting the third cap with a hammer.

11. The method of claim 1 further comprising the steps of:
    inserting a distal end of a cervical cutter into the sheath hollow core and into the mammal, the cervical cutter having a proximal end with a handle thereon and a drill bit on a tip of a distal end of the cervical cutter; and
    rotating the cervical cutter upon the drill bit reaching a point of cutting within the mammal.

12. The method of claim 11, wherein inserting the deburrment cutter distal end into the sheath hollow core includes passing the deburrment cutter over a guide wire passed through a hollow core of the deburrment cutter.

13. The method of claim 1 further comprising the steps of:
    inserting a distal end of a deburrment cutter into the sheath hollow core and into the mammal such that the distal end protrudes from the sheath distal end at a desired location within the mammal, the deburrment cutter having a proximal end with a third cap attached thereto and burr on the protruding distal end; and
    rotating the burr at the desired location by turning the attached third cap.

14. The method of claim 13 further comprising the steps of:
    removing the third cap from the deburrment cutter while the deburrment cutter is in the sheath hollow core and while the sheath is in the mammal neck;
    receiving the proximal end of the deburrment cutter within a hollow core of an impactor while the deburrment cutter is in the sheath hollow core and while the sheath is in the mammal neck such that the impactor slides over the deburrment cutter and abuts against the first cap on the sheath, the impactor hollow core having a diameter greater than the deburrment cutter; and
    placing an impact force onto the impactor so as to transfer said impact force to the sheath and not to the deburrment cutter.

15. The method of claim 1 further comprising the steps of:
    inserting a grasping end of pituitaries into the sheath hollow core and into the mammal.

16. A method for performing an anterior cervical discectomy within a neck of a mammal comprising the steps of:
    passing a distal end of a sheath into the neck of the mammal, the sheath having a hollow core and a proximal end with a first cap thereon;
    attaching a second cap to a deburrment cutter on a proximal end of the deburrment cutter, the deburrment cutter also having a distal end with a burr thereon;

inserting the deburrment cutter distal end into the sheath hollow core and into the mammal such that the distal end protrudes from the sheath distal end at a desired location within the mammal;

rotating the burr at the desired location by turning the attached second cap;

removing the second cap from the deburrment cutter while the deburrment cutter is in the sheath hollow core and while the sheath is in the mammal neck;

receiving the proximal end of the deburrment cutter within a hollow core of an impactor while the deburrment cutter is in the sheath hollow core and while the sheath is in the mammal neck, such that the impactor slides over the deburrment cutter and abuts against the first cap on the sheath, the impactor hollow core having a diameter greater than the deburrment cutter; and placing an impact force onto the impactor so as to transfer said impact force to the sheath and not to the deburrment cutter.

17. The method of claim 16, wherein inserting the deburrment cutter distal end into the sheath hollow core includes passing the deburrment cutter over a guide wire passed through a hollow core of the deburrment cutter.

18. The method of claim 16, wherein passing the sheath distal end into the mammal neck includes inserting the sheath anterior of the mammal neck at an angle of about 45 degrees such that the sheath passes through the neck just behind a trachea and an esophagus within the neck and just medial to a carotid and a jugular within the neck.

* * * * *